US00RE35071E

United States Patent [19]

Lewis et al.

[11] E Patent Number: Re. 35,071

[45] Reissued Date of Patent: Oct. 24, 1995

[54] OPTIMUM FIXED ANGLE CENTRIFUGE ROTOR

[75] Inventors: Mark L. Lewis, Burlingame; Thomas D. Sharples, Atherton; Stephen E. Little, Cupertino, all of Calif.

[73] Assignee: Beckman Instruments, Inc., Fullerton, Calif.

[21] Appl. No.: 80,455

[22] Filed: Jun. 18, 1993

Related U.S. Patent Documents

Reissue of:

[64] Patent No.: 5,024,646
Issued: Jun. 18, 1991
Appl. No.: 418,060
Filed: Oct. 6, 1989

[51] Int. Cl.[6] ..... B04B 5/02

[52] U.S. Cl. ..... 494/16; 494/37

[58] Field of Search ..... 494/16, 17, 18, 494/19, 20, 21, 37, 85, 81, 93; 210/781, 782, 360.1; 422/72

[56] References Cited

U.S. PATENT DOCUMENTS

| | | | |
|---|---|---|---|
| 3,998,383 | 12/1976 | Romanauskas et al. | 233/26 |
| 4,015,775 | 4/1977 | Rohde | 233/26 |
| 4,290,550 | 9/1981 | Chulay et al. | 233/26 |
| 4,301,963 | 11/1981 | Nielsen | 233/26 |
| 4,304,356 | 12/1981 | Chulay et al. | 233/26 |
| 4,509,940 | 4/1985 | Romanauskas | 494/16 |
| 4,690,670 | 9/1987 | Nielsen | 494/16 |
| 4,692,137 | 9/1987 | Anthony | 494/85 |
| 4,824,429 | 4/1989 | Keunen | 494/16 |

FOREIGN PATENT DOCUMENTS

| | | | |
|---|---|---|---|
| WO85/05567 | 12/1985 | European Pat. Off. | B04B 5/04 |
| 2435714 | 4/1980 | France . | |

OTHER PUBLICATIONS

Flamm, W. G. et al.; "Density–Gradient Centrifugation of DNA In a Fixed–Angle Rotor, A Higher Order of Resolution" *Biochimica et Biophysica ACTA*, 129 (1966) pp. 310–317.

Fisher, W. D. et al.; "Density Gradient Centrifugation in Angle–Head Rotors"; *Analytical Biochemistry* 9 (1964) pp. 477–482.

Masket, A. Victor; "A Quantity Type Rotor for the Ultracentrifuge"; *Review of Scientific Instruments* pp. 277–279 (undated).

*Primary Examiner*—Robert W. Jenkins
*Attorney, Agent, or Firm*—William H. May; Gary T. Hampson

[57] ABSTRACT

A centrifuge rotor and method for gradient density separation which supports a generally cylindrical volume of sample solution with its axis inclined to the spin axis at an angle which is optimized for maximum separation efficiency while reducing contamination by undesirable centrifugates upon reorientation of the desirable centrifugates. *The sample solution is contained in a centrifuge tube which is closed at its top end by a top portion which is supported by a support cap. The undesirable centrifugates are pelleted to the end corners of the inclined centrifuge tube. The rotor and method are particularly adapted, for example, for separation of nucleic acid into plasmid DNA and chromosomal DNA by density gradient centrifugation.* The optimum angle is determined based on the relationship $\theta = \mathrm{Tan}^{-1}\,(D/15L)^{0.5}$ where D and L are respectively the diameter and length of the cylindrical volume of the sample solution and θ is the angle of inclination.

40 Claims, 2 Drawing Sheets

OPTIMUM FIXED ANGLE CENTRIFUGE ROTOR

Matter enclosed in heavy brackets [ ] appears in the original patent but forms no part of this reissue specification; matter printed in italics indicates the additions made by reissue.

BACKGROUND OF THE INVENTION

1. Field of the Invention

The present invention relates to centrifuge rotors and, more particularly, to centrifuge rotors which support centrifuge tubes at an angle to the spin axis for density gradient separation.

2. Description of Related Art

Essentially, a centrifuge is a device for separating particles suspended in a solution. A centrifuge includes a rotor which supports several containers of sample solution for rotation about a common spin axis. As the rotor spins in the centrifuge, centrifugal force is applied to each particle in the sample solution; each particle will sediment at a rate which is proportional to the centrifugal force experienced by the particle. Centrifugal force is dependent on the mass of the particle, the rotational speed of the rotor, and the distance of the particle from the spin axis. The viscosity and density of the sample solution also affects the sedimentation rate of each individual particle. At a given centrifugal force, density and liquid viscosity, the sedimentation rate of the particle is proportional to its molecular weight, and the difference between its density and the density of the solution.

One of many methods of centrifugal separation is by isopycnic separation, a form of density gradient centrifugation. Such a method permits the separation of several or all of the particles in a sample mixture according to their densities. The method involves a supporting column of fluid (hereinafter referred to as "density gradient fluid") whose density encompasses the whole range of densities of the sample particles and increases toward the bottom of the centrifuge tube. The density gradient fluid typically consists of one or more suitable low molecular weight solute in a solvent in which the sample particles can be suspended. Upon centrifugation, each particle will sediment only to the position in the centrifuge tube at which the density of the density gradient fluid is equal to its own density, and there it will remain. The isopycnic technique, therefore, separates particles into zones or bands solely on the basis of their density differences, independent of time.

Density gradients have been used extensively in the separation and purification of a wide variety of biological materials. For example, nucleic acids have been studied extensively by density gradient methods. For purposes of discussion, isopycnic banding type density gradient centrifugation techniques will be discussed below in connection with DNA banding. In the past, cesium chloride has been successfully used as the density gradient fluid in DNA banding. Under the influence of centrifugal force, the cesium chloride salt redistributes in the centrifuge tube so as to form the required concentrations to create a density gradient. This is often referred to as the self-generating gradient technique in which a continuous density gradient is obtained at equilibrium when the diffusion of cesium chloride towards the spin axis balances the sedimentation away from the spin axis at each radial location along the centrifuge tube.

A nucleic acid may be separated into plasmid DNA and chromosomal DNA by using the cesium chloride density gradient. In addition RNA and proteins in the nucleic acid are separated. The plasmid DNA is separated from the chromosomal DNA by their differences in buoyant density, the plasmid DNA being more dense. More particularly, the plasmid DNA and chromosomal DNA are isolated into isopycnic bands at different radial positions from the spin axis, the plasmid DNA being more dense forms a band at a larger radial distance from the spin axis. In addition, RNA which is heavier forms a pellet at the furthermost radial location in the centrifuge tube and proteins being the lightest particles are "floated" to the innermost radial position close to the spin axis to form a pellet. The RNA and protein are usually not of interest to DNA studies and undesirable as they are a source of contamination of the DNA bands.

In most laboratories, density gradient centrifugation of nucleic acids is carried out using conventional swinging-bucket, fixed-angle and vertical tube rotors. In a swinging bucket rotor, centrifuge tubes are hingedly supported. As the rotor rotates, the centrifuge tubes swing radially outward from a vertical position to a horizontal position. After a period of time, as shown in FIG. 1A, the nucleic acid contained in the centrifuge tubes 18 separates into the plasmid DNA 10 and chromosomal DNA 12 bands as well as RNA 14 and protein 16 pellets. Since the density gradient is formed radially outward from the spin axis, the bands are parallel to the spin axis 20. After centrifugation, the centrifuge tubes 18 return to their vertical position as shown in FIG. 1B. The fractionated DNA bands are extracted from each centrifuge tube using suitable tools. It has been found that nucleic acid separation carried out using a swinging bucket rotor requires long run time to allow sedimentation to take place along the length of the centrifuge tube as indicated by arrow 19. Furthermore, it requires high rotor speeds in order to provide enough centrifugal forces to effect separation of the components located close to the spin axis 20. For a given maximum radial tube position from the spin axis $r_{max}$, the average radial distance from the spin axis $r_{average}$ is substantially shorter thus giving rise to a smaller overall centrifugal force at a given rotor speed.

In a vertical tube rotor, sealed centrifuge tubes have been used in the past such as the Quick Seal® tubes developed by Beckman Instruments, Inc. as shown in FIG. 2A are supported vertically during centrifugation. Upon centrifugation, the isopycnic plasmid 22 and chromosomal 24 bands and protein 26 and RNA 28 pellets are oriented vertically or parallel to the spin axis 30. After centrifugation, the DNA bands 22 and 24 reorientate into horizontal layers as shown in FIG. 2B. The RNA and protein pellets 26 and 28, however, tend to remain stuck to the centrifuge tube wall. It will be appreciated that the transition of the DNA bands during reorientation from the vertical position shown in FIG. 2A to the horizontal position shown in FIG. 2B causes intermixing of the DNA bands and the pellets as the DNA bands 22 and 24 sweep across the protein and RNA pellets 26 and 28, thereby resulting in contamination of the DNA bands. Furthermore, the protein and DNA pellets may detach from the tube walls when the rotor is at rest and mix the contents in the tube. Precentrifugation clean-up steps such as differential centrifugation will be necessary to remove the protein and RNA particles prior to density gradient separation of DNA bands in order to avoid such contamination. The additional clean-up steps are time consuming. The advantage of vertical tube rotor over swinging bucket rotor, however, is in the increased effectiveness for density gradient centrifugation which in many instances yielding separations in considerably less time than achieved in swinging bucket rotors operating either at the same speed or higher speeds. The centrifuge tubes being vertical in a vertical tube rotor are disposed at a larger average radial distance $r_{average}$ from the spin axis when compared to a swinging bucket rotor having the same maximum radial tube position $r_{max}$. Also, the particle sedimentation path length radially outward across the width of the centrifuge tube as indicated by arrow 31 is considerably less than that along the length of the centrifuge tube in the swinging bucket rotor as shown in FIG. 1B.

The fixed angle rotor is effectively a compromise between the swinging bucket rotor and the vertical tube rotor. The centrifuge tubes 32 in a fixed angle rotor are supported at a fixed angle in the range of 20°–40° to the spin axis during centrifugation, as illustrated in FIG. 3A. Isopycnic DNA bands 34 and 36 and pellets 38 and 40 are formed parallel to the spin axis upon centrifugation. Upon termination of centrifugation and removal of the tubes 32 from the rotor, the DNA bands 34 and 36 reorientate to a horizontal position as shown in FIG. 3B. The probability of contamination of the isopycnic bands 34 and 36 during reorientation is reduced in the case of the fixed angle rotor. However, for a given rotor speed and maximum radius $r_{max}$, fixed angle rotors are inherently less efficient than vertical tube rotors due to shorter average centrifuge tube radial distance $r_{average}$ from the spin axis 42 and increased sedimentation path length as indicated by arrow 43 for a given tube size.

SUMMARY OF THE INVENTION

The present invention is directed to a centrifuge rotor optimized for density gradient separation which supports a generally cylindrical volume of sample solution at an angle as close to the vertical as possible to maximize separation efficiency while avoiding contamination of isopycnic bands during reorientation upon termination of centrifugation, and a method of obtaining the optimized angle.

According to the present invention, the angle of inclination of the sample volume to the spin axis is determined according to the physical dimension of the sample volume. More particularly, for a cylindrical sample volume, contained for example in a centrifuge tube, having a given diameter D and length L, the angle of inclination is dependent on the $\mathrm{Tan}^{-1}\,(D/15L)^{0.5}$. Conversely, for a given angle of inclination, the size of centrifuge tubes that should be used to optimize separation efficiency and minimize contamination of separated isopycnic bands can be determined.

DESCRIPTION OF THE ILLUSTRATED EMBODIMENTS

The following description is of the best presently contemplated mode of carrying out the invention. This description is made for the purpose of illustrating the general principles of the invention and should not be taken in a limiting sense. The scope of the invention is best determined by reference to the appended claims.

Figure 1A:
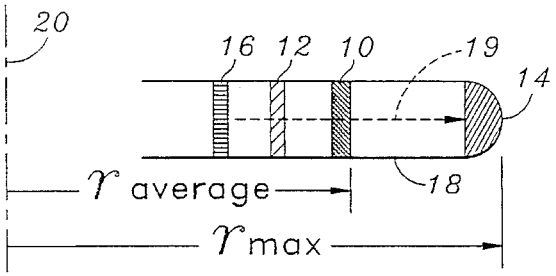
FIG. 1A (PRIOR ART)
FIGS. 1A and B illustrate the orientation of isopycnic bands during and after centrifugation in the case of a swinging bucket rotor.
Figure 1B:
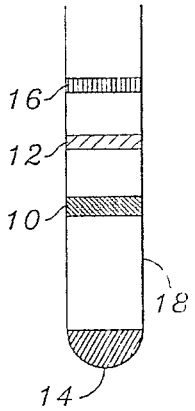
(PRIOR ART) FIG. 1B
Figure 2A:
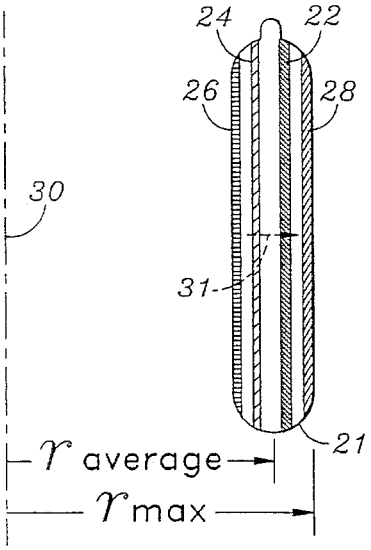
(PRIOR ART) FIG. 2A
FIGS. 2A and B illustrate the orientation of isopycnic bands during and after centrifugation in the case of a vertical tube rotor.
Figure 2B:
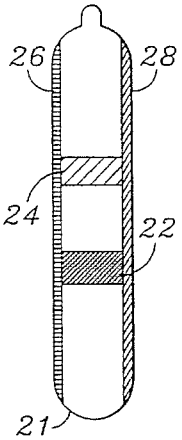
(PRIOR ART) FIG. 2B
Figure 3B:
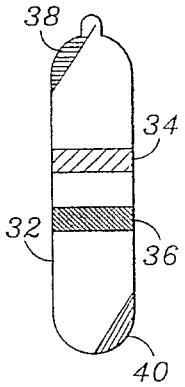
(PRIOR ART) FIG. 3B
FIGS. 3A and B illustrate the orientation of isopycnic bands during and after centrifugation in the case of a fixed angle rotor.
Figure 3A:
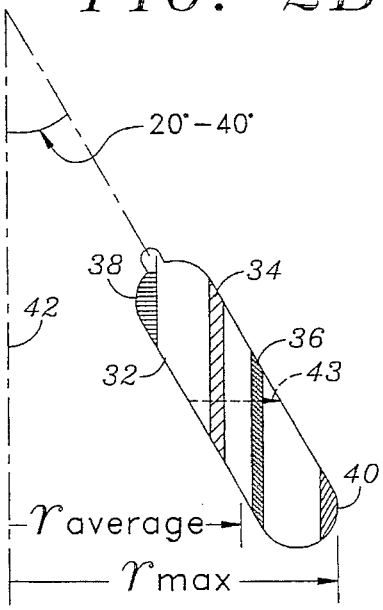
(PRIOR ART) FIG. 3A
Figure 4:
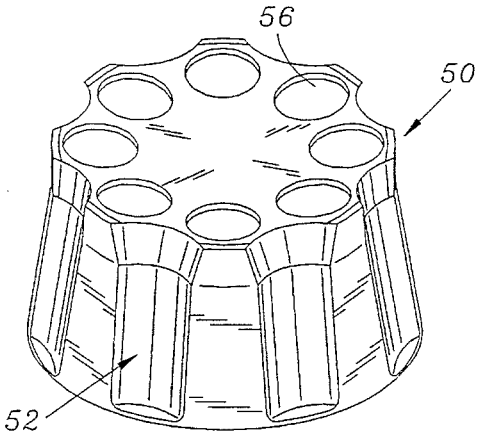
FIG. 4 is a perspective view of an optimized fixed angle rotor according to one embodiment of the present invention.

FIG. 4 shows a perspective view of a fixed angle centrifuge rotor 50 optimized for density gradient separation according to one embodiment of the present invention. The rotor 50 has a generally cylindrical body and a plurality of circumferentially spaced bores or cavities 56, each adapted to retain a sample containing tube during centrifugation. Scallops 52 are formed on the cylindrical surface between adjacent cavities to reduce the overall mass of the rotor. Referring to the view shown in FIG. 5, base 52 of the rotor is shaped to fit on a spindle of a drive motor (not shown) for rotation about a spin axis 54.

The cavities 56 are formed at an oblique angle θ with respect to the spin axis 54 of the rotor 50, the bottom of the cavities being further away from the spin axis 54 than the cavity opening. With this arrangement, the horizontally acting centrifugal force has components acting both radially and axially in each cavity 56, with the axial force component urging the sample toward the bottom, or outer, end of the cavity 56. The angle θ which optimizes separation efficiency and reduces contamination is determined by a method to be discussed in detail below.

Figure 5:
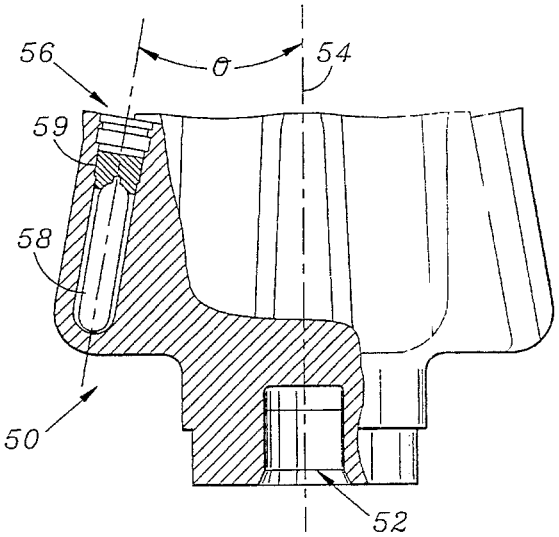
FIG. 5 is a side view of the rotor of FIG. 4 partially broken away to show a sectional view of the sample containing tube cavity.

Inserted in each cavity 56 is a thin-walled sample containing tube 58 and a support cap 59 engaging the top of the tube. The tube 58 shown is a Quick-Seal® tube of the type disclosed and patented in U.S. Pat. No. 4,301,963 commonly assigned to the assignee of the present invention and is incorporated by reference herein. The top and bottom portions of the tube 58 is shown in FIG. 5 to be hemispherical. These portions may be shaped differently, e.g. bell-shaped or conical, and the tube facing surface of the support cap is shaped accordingly. In the center of the top portion of the tube 58 is a projection formed initially as a tube-like extension through which the fluid sample is inserted into the tube 58, and then hermetically sealed by a suitable process, such as heat fusion. The sealed end of the tube 58 is closer to the spin axis than the majority of the tube and its fluid contents. The body of the tube 58 is generally cylindrical having internal diameter D and length L. It is apparent that the dimensions of the substantially cylindrical volume of sample solution enclosed by the tube 58 is equal to the internal dimensions of the tube 58. The tube 58 is substantially filled with the sample solution. The cap 59 is free to slide along the cavity to provide support to the top portion of the tube 58 against hydrostatic pressure of the contents in the tube as well as deformation caused by centrifugation forces. The cap is referred to as a floating cap which has been described and patented in U.S. Pat. No. 4,304,356 commonly assigned to the assignee of the. present invention and is incorporated by reference herein. A locking cap (not shown) may be screwed into the opening of the cavity to securely retain the tube 58 and cap 59 within the cavity 56.

It is envisioned that other types of tubes, seals and support caps could be utilized in the rotor 50 for density gradient centrifugation. As an example of density gradient separation, isopycnic banding of DNA from nucleic acid will be discussed below.

Figure 6A:
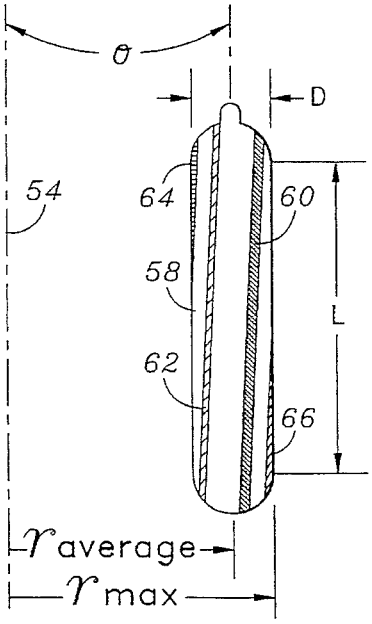
FIGS. 6A and B illustrate the orientation of isopycnic bands during and after centrifugation in the case of an optimized fixed angle rotor according to the present invention.

Referring to FIG. 6A, the nucleic acid contained in the centrifuge tube 58 is separated into plasmid 60 and chromosomal 62 DNA bands and protein 64 and RNA 66 pellets upon centrifugation. The bands and pellets are in a vertical orientation as a result of radial centrifugal forces. Cesium Chloride self-generating density gradient solution may be used to create the density gradient for obtaining the isopycnic bands.

Figure 6B:
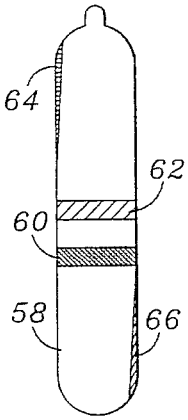

Upon the termination of centrifugation and removal of the tube 58 from the rotor 50, the isopycnic DNA bands 60 and 62 reorientate into a horizontal orientation as shown in FIG. 6B. The protein and RNA pellets do not reorientate but remain in their original position against the end corners of the centrifuge tube.

According to the present invention, the cavities 56 are formed such that the dimensions of the volume of sample solution, in this case the internal dimensions L and D of the thin-walled centrifuge tube 58 designed for use with the rotor, and the angle of inclination of the tube axis θ approximately satisfy the relationship:

$$\theta = \mathrm{Tan}^{-1}\,(D/15L)^{0.5} \qquad 1$$

This relationship is determined empirically. For thin-walled tubes, e.g. 10–20 mils wall thickness, the outside diameter may be applied to the relationship (1) without substantially affecting the results. It is noted that the top and bottom hemispherical portions of the tube 58 beyond the length L have been "ignored" in formulating the empirical relationship (1). The reason being that most of the pellets 64 and 66 do not accumulate within these hemispherical portions, at least at small θ. Thus, the hemispherical ended tube 58 can effectively be treated as a flat bottom cylinder with length L to a close approximation. It can be seen that for θ that is small, e.g. less than 10°, the relationship (1) can be approximated as:

$$\theta = (D/15L)^{0.5} \qquad 2$$

where θ is measured in radians. Small departures from the relationship may be necessary for manufacturing convenience and design constraints.

Examples of actual fixed angle rotors made in which the angle of inclination θ of the sample volume to the spin axis for given sample volume dimensions (approximately equal to the dimensions of thin-walled centrifuge tube) approximately satisfy the relationship (1) and comparisons to the theoretical θ values according to the relationship (1) are given below (the D and L listed below are nominal outside dimensions of actual thin-walled centrifuge tubes which approximate internal dimensions):

| Example | L | D | theoretical θ in accordance with relationship (1) | θ in actual rotor made |
|---|---|---|---|---|
| I. | 2.5" | 0.625" | 7.4° | 7.5° |
| II. | 1.6" | 0.5" | 8.25° | 8° |
| III. | 1" | 0.5" | 10.45° | 9° |

It can be seen that Examples I and II satisfy the relationship (1) quite closely within a few percent deviation. For Example III, the deviation is approximately 14% due to physical constraints necessary to accommodate manufacturing convenience and the more significant effect of the hemispherical top and bottom portions of the tube 58 which have not been taken into account in the relationship (1).

In the past, tubes of similar dimensions have been used in fixed angle rotors having angle of inclinations between 20° to 40°. These tubes and rotors do not satisfy the relationship (1). For rotors with θ within the range from 20° to 40°, the D/L ratios should have been approximately within the range from 1.8 to 7.31 in order to satisfy the relationship (1). Tubes with such D/L ratios are rather squat and are not believed to have been used in the past.

It has been found that using the centrifuge rotor which has centrifuge tube axis inclined at an angle θ to the spin axis that approximately satisfies the relationship (1), isopycnic 60 and 62 bands are obtained which do not come into contact with the pellets 64 and 66 upon reorientation as shown in FIG. 5. Moreover, a high separation efficiency is obtained with the rotor having such an angle of inclination since the average radius $r_{average}$ is large for a given maximum radius. Thus, the rotor speed can be kept well below the limit above which the rotor will fail due to overstressing. Furthermore, gradient material crystallization, a process where the density gradient fluid crystallizes causing sudden density change as a result of high centrifugal force experienced at the furthermost radial position $r_{max}$ of the centrifuge tube, which would cause rotor damage can be avoided. By keeping the $r_{max}$ close to $r_{average}$, the centrifugal forces experienced at $r_{average}$ and $r_{max}$ will not be substantially different for a given average centrifugal force. Still further, precentrifugation clean-up steps for removing the undesirable RNA and protein particles are not necessary in order to avoid contamination of the plasmid and chromosomal DNA bands. Thus it can be seen that by using the relationship (1) to determine the angle of inclination of the centrifuge tube axis, contamination of the isopycnic bands during reorientation can be avoided without compromising the separation efficiency of the rotor.

It is envisioned that for some centrifugation applications, smaller size centrifuge tubes could be utilized in the rotor 50 having cavities designed for receiving larger size tubes 58. For example, a tube with smaller diameter may be supported in the cavity by use of an cylindrical adapter as described in U.S. Pat. No. 4,692,137 commonly assigned to the assignee of the present invention and incorporated by reference herein. A shorter centrifuge tube could also be utilized by providing additional spacers between the supporting cap and the top end of the centrifuge tube as described in U.S. Pat. No. 4,290,550 commonly assigned to the assignee of the present invention and incorporated by reference herein. Further, the centrifuge tube need not be completely filled. It is theorized that as long as the length L and diameter D of the volume of sample solution and the angle of inclination θ of the volume to the spin axis satisfy the relationship (1), the advantage of obtaining maximum separation efficiency and reducing contamination in accordance with the present invention can be realized.

From the foregoing, it could be summarized that the dimension of the cylindrical volume of sample solution is relevant to the concept of the present invention. The specific structure used for containing the solution is not of critical importance to the practice of the present invention. It is envisioned that fluid to be centrifuged could be contained in the centrifuge rotor cavity without using a centrifuge tube, although the practicality of this has not been explored at this time.

While the invention has been described with respect to the illustrated embodiments in accordance therewith, it will be apparent to those in the art that various modifications and improvements may be made without departing from the scope and spirit of the invention. Accordingly, it is to be understood that the invention is not to be limited by the specific illustrated embodiments, but only by the scope of the appended claims.

[I] *We* claim:

1. A centrifuge rotor comprising:

a rotor body rotatable about a spin axis; and means formed on the rotor body for supporting a generally cylindrical volume of diameter D and length L of sample solution for centrifugation about the spin axis such that the cylindrical volume is inclined with its axis at an angle θ to the spin axis, where θ, D and L approximately satisfy the relationship:

$$\theta=\mathrm{Tan}^{-1}(D/15L)^{0.50}$$

2. A centrifuge rotor as in claim 1 wherein θ is approximately 10.45° or less.

3. A centrifuge rotor as in claim 2 wherein θ deviates from the angle calculated from said relationship at given D and L by approximately 14% or less.

4. A centrifuge rotor as in claim 3 wherein θ is approximately 7.5°.

5. A centrifuge rotor as in claim 3 wherein θ is approximately 8.0°.

6. A centrifuge rotor as in claim 3 wherein θ is approximately 9.0°.

7. A centrifuge rotor as in claim 1 wherein the means for supporting comprises the rotor body having a cavity inclined at angle θ to the spin axis and a sample container which is shaped to be received in the cavity.

8. A centrifuge rotor as in claim 7 wherein the sample container is a sealed, generally cylindrical shaped centrifuge tube substantially filled with the sample solution.

9. A centrifuge rotor as in claim 8 wherein the sample solution comprises a density gradient fluid and a sample to be centrifuged by density gradient separation.

10. A centrifuge rotor as in claim 9 wherein the sample is nucleic acid to be separated into at least plasmid DNA and chromosomal DNA isopycnic bands.

11. A centrifuge rotor as in claim 8 wherein the means for supporting further comprises a floating support cap for supporting the top of the centrifuge tube.

12. In a centrifuge rotor for density gradient centrifugation of a generally cylindrical volume of diameter D and length L of sample solution about a spin axis, the cylindrical volume being supported by the rotor such that its axis is inclined at an angle θ to the spin axis where L, D and θ approximately satisfy the relationship:

$$\theta=\mathrm{Tan}^{-1}(D/15L)^{0.5}$$

13. A centrifuge rotor comprising:

a rotor body defining therein a plurality of cavities distributed axial symmetrically about a spin axis, each cavity having its longitudinal axis inclined at an angle θ to the spin axis; and at least one container for containing sample solution to be centrifuged, wherein each cavity is shaped to receive the container and the container has an internal space for containing a generally cylindrical volume of sample solution of diameter D and length L, where θ, D and L approximately satisfy the relationship:

$$\theta=\mathrm{Tan}^{-1}(D/15L)^{0.5}$$

14. A method of making a centrifuge rotor for density gradient centrifugation comprising the steps of:

providing a rotor body rotatable about a spin axis;

forming support on the rotor body for supporting a generally cylindrical volume of diameter D and length L of sample solution such that the axis of the volume is inclined at an angle θ to the spin axis, where D, L and θ approximately satisfy the relationship:

$$\theta=\mathrm{Tan}^{-1}(D/15L)^{0.5}$$

15. A method of density gradient centrifugation comprising the steps of:

providing a rotor rotatable about a spin axis;

providing a sample solution;

supporting on the rotor a generally cylindrical volume of diameter D and length L of the sample solution such that its axis is nclined at an angle θ to the spin axis, where D, L and θ approximately satisfy the relationship:

$$\theta=\mathrm{Tan}^{-1}(D/15L)^{0.5}; \text{ and}$$

rotating the rotor about the spin axis to cause centgrifugation.

16. A method as in claim 15 wherein the supporting step comprises forming a cavity inclined at angle θ in the rotor and providing a sample container which is shaped to be received in the cavity.

17. A method as in claim 16 wherein the sample container provided is a sealed, generally cylindrical shaped centrifuge tube which is substantially filed with sample solution.

18. A method as in claim 17 wherein the sample solution provided comprises a density gradient fluid and a sample to be centrifuged by density gradient separation.

19. A method as in claim 18 wherein the sample is nucleic acid to be separated into at least plasmid DNA and chromosomal DNA isopycnic bands.

20. A method as in claim 15 wherein θ is approximately 10.45° or less.

*21. A centrifuge rotor particularly adapted for density gradient centrifugal separation of a sample comprising:*

*a rotor body having therein a plurality of cavities distributed symmetrically about a spin axis of said rotor body, each cavity having its longitudinal axis inclined at an angle θ to said spin axis and adapted to hold a centrifuge tube which has a cylindrical sidewall for containing a generally cylindrical volume of diameter D and length L of a sample mixture in a density gradient solution to be centrifuged;*

*said cavities being configured in the rotor body where θ, L and D are such that, upon centrifugation at least first and second pellets of first and second materials are formed at extreme radial corners of the inclined centrifuge tube and extending along the cylindrical sidewall of the centrifuge tube and at least one isopycnic band of a third material is formed vertically in the density gradient solution between the first and second pellets, and upon termination of centrifugation the pellets are stuck to said corners and sidewall of the centrifuge tube and the isopycnic band reorientates into a horizontal orientation with its periphery touching the sidewall of the centrifuge tube but slightly away from the first and second pellets,*

*whereby the average centrifugal force on said sample mixture is maximized during centrifugation but there is no contact between the third material and either the first and second materials upon horizontal reorientation of the third material upon termination of centrifugation.*

22. A centrifuge rotor as in claim 21 wherein θ, D and L approximately satisfy the relationship:

$$\theta = Tan^{-1}(D/15L)^{0.5}$$

23. A centrifuge rotor as in claim 21 wherein the sample mixture is nucleic acid to be separated into at least plasmid DNA and chromosomal DNA isopycnic bands.

24. A centrifuge rotor as in claim 21 wherein θ is approximately 10.45° or less.

25. A centrifuge rotor as in claim 24 wherein θ is approximately 7.5°.

26. A centrifuge rotor as in claim 24 wherein θ is approximately 8.0°.

27. A centrifuge rotor as in claim 24 wherein θ is approximately 9.0°.

28. A centrifuge rotor as in claim 21 wherein the rotor includes means for supporting a top portion which extends from the cylindrical sidewall of the centrifuge tube and closes top end of the centrifuge tube, said top portion having at its center a tube-like extension through which a sample mixture can be inserted.

29. A method of density gradient centrifugal separation of a sample comprising the steps of:

providing a sample mixture in a density gradient solution;

providing a centrifuqe tube which has a cylindrical sidewall for containing a generally cylindrical volume of diameter D and length L of the sample mixture and density gradient solution to be centrifuged;

providing a rotor having therein a plurality of cavities distributed symmetrically about a spin axis of said rotor, each cavity having its longitudinal axis inclined at an angle θ to said spin axis and adapted to hold the centrifuge tube, said cavities being configured in the rotor where θ, L and D are selected such that, upon centrifugation at least first and second pellets of first and second materials are formed at extreme radial corners of the inclined centrifuge tube and extending along the cylindrical sidewall of the centrifuge tube and at least one isopycnic band of a third material is formed vertically in the density gradient solution between the first and second pellets, and upon termination of centrifugation the pellets are stuck to said corners and sidewall of the centrifuge tube and the isopycnic band reorientates into a horizontal orientation with its periphery touching the sidewall of the centrifuge tube but slightly away from the first and second pellets;

placing the centrifuge tube and its contents into the cavity; and rotating the rotor about the spin axis to effect centrifugal separation of the sample mixture to form at least one isopycnic band of said third material, whereby the average centrifugal force on said sample mixture is maximized during centrifugation but there is no contact between the third material and either the first and second materials upon horizontal reorientation of the third material upon termination of centrifugation.

30. A method as in claim 29 wherein θ, D and approximately satisfy the relationship:

$$\theta = Tan^{-1}(D/15L)^{0.5}$$

31. A method as in claim 29 wherein the sample mixture is nucleic acid to be separated into at least plasmid DNA and chromosomal DNA isopycnic bands.

32. A method as in claim 29 wherein θ is approximately 10.45° or less.

33. A method as in claim 32 wherein θ is approximately 7.5°.

34. A method as in claim 32 wherein θ is approximately 8.0°.

35. A method as in claim 32 wherein θ is approximately 9.0°.

36. A method as in claim 29 wherein the centrifuge tube has a top portion which extends from the cylindrical sidewall of the centrifuge tube and closes top end of the centrifuge tube, said top portion having at its center a tube-like extension through which a sample mixture can be inserted, and wherein the method further including the step of providing means for supporting said top portion of the centrifuge tube after it is placed in the cavity.

37. A method of density gradient centrifugal separation of a nucleic acid sample mixture into at least plasmid DNA and chromosomal DNA isopycnic bands comprising the steps of:

providing a nucleic acid sample mixture in a density gradient solution;

providing a centrifuge tube, said centrifuge tube having a cylindrical sidewall for containing a generally cylindrical volume of diameter D and length L of the sample mixture and density gradient solution to be centrifuged, and a top portion which extends from the cylindrical sidewall of the centrifuge tube and closes top end of the centrifuge tube, said top portion having at its center a tube-like extension through which a sample mixture can be inserted;

providing a rotor having therein a plurality of cavities distributed symmetrically about a spin axis of said rotor, each cavity having its longitudinal axis inclined at an angle θ to said spin axis and adapted to hold the centrifuge tube, said cavities being configured in the rotor where θ, L and D are selected such that, upon centrifugation at least first and second pellets of first and second materials are formed at extreme radial corners of the inclined centrifuge tube and extending along the cylindrical sidewall of the centrifuge tube and at least a plasmid DNA isopycnic band and a chromosomal DNA isopycnic band are formed vertically in the density gradient solution between the first and second pellets, and upon termination of centrifugation the pellets are stuck to said corners and sidewall of the centrifuge tube and said plasmid DNA and chromosomal DNA isopycnic bands reorientate into a horizontal orientation with their peripheries touching the sidewall of the centrifuge tube but slightly away from the first and second pellets;

placing the centrifuge tube and its contents into the cavity;

providing means for supporting said top portion of the centrifuge tube after it is placed in the cavity; and rotating the rotor about the spin axis to effect centrifugal separation of the sample mixture to form the plasmid DNA and chromosomal DNA bands, whereby the average centrifugal force on said sample mixture is maximized during centrifugation but there is no contact between the plasmid DNA or chromosomal DNA bands and the first and second pellets upon horizontal reorientation of the third material upon termination of centrifugation.

38. A method as in claim 37 wherein θ is approximately 10.45° or less.

39. A method of density gradient centrifugal separation of

*a sample mixture into at least one isopycnic band comprising the steps of:*

*providing a sample mixture in a density gradient solution;*

*providing a centrifuge tube, said centrifuge tube having a cylindrical sidewall for containing a generally cylindrical volume of the sample mixture and density gradient solution to be centrifuged, and a top portion which extends from the cylindrical sidewall of the centrifuge tube and closes top end of the centrifuge tube, said top portion having at its center a tube-like extension through which a sample mixture can be inserted;*

*providing a rotor having therein a plurality of cavities distributed symmetrically about a spin axis of said rotor, each cavity having its longitudinal axis inclined at an angle less than 10.45° to said spin axis and adapted to hold the centrifuge tube;*

*placing the centrifuge tube and its contents into the cavity;*

*providing means for supporting said top portion of the centrifuge tube after it is placed in the cavity; and*

*rotating the rotor about the spin axis to effect centrifugal separation of the sample mixture to form at least one isopycnic band,*

*whereby the average centrifugal force on said sample mixture is maximized upon centrifugation and mixing of the isopycnic band and other pelleted substance can be avoided upon termination of centrifugation.*

*40. A centrifuge rotor particularly adapted for density gradient centrifugal separation of a sample mixture into at least one isopycnic band, comprising:*

*a rotor body having therein a plurality of cavities distributed symmetrically about a spin axis of said rotor body, each cavity having its longitudinal axis inclined at an angle less than 10.45° to said spin axis and adapted to hold a centrifuge tube which has a cylindrical sidewall for containing a generally cylindrical volume of a sample mixture in a density gradient solution to be centrifuged and a top portion which extends from the cylindrical sidewall of the centrifuge tube and closes top end of the centrifuge tube, said top portion having at its center a tube-like extension through which a sample mixture can be inserted; and*

*means for supporting said top portion of the centrifuge tube after it is placed in the cavity;*

*whereby the average centrifugal force on said sample mixture is maximized during centrifugation and mixing of the isopycnic band and other pelleted substance can be avoided upon termination of centrifugation.*

* * * * *

UNITED STATES PATENT AND TRADEMARK OFFICE

CERTIFICATE OF CORRECTION

PATENT NO. : Re. 35,071

DATED : October 24, 1995

INVENTOR(S) : Mark L. Lewis, Thomas D. Sharples and Stephen E. Little

It is certified that error appears in the above-indentified patent and that said Letters Patent is hereby corrected as shown below:

Column 9, line 60 after "and" insert --L--

Signed and Sealed this

First Day of December, 1998

*Attest:*

*Attesting Officer*

BRUCE LEHMAN

*Commissioner of Patents and Trademarks*